United States Patent [19]
Christianson et al.

[11] Patent Number: 5,131,997
[45] Date of Patent: Jul. 21, 1992

[54] CAPILLARY ZONE ELECTROPHORESIS CASSETTE

[75] Inventors: John A. Christianson, Mountain View; Douglass McManigill, Palo Alto; James E. Young, La Honda, all of Calif.

[73] Assignee: Hewlett-Packard Company, Palo Alto, Calif.

[21] Appl. No.: 522,278

[22] Filed: May 11, 1990

[51] Int. Cl.⁵ ................... G01N 27/26; B01D 57/02
[52] U.S. Cl. ............................ 204/299 R; 204/180.1
[58] Field of Search ...................... 204/299 R, 180.1

[56] References Cited

U.S. PATENT DOCUMENTS

| | | | |
|---|---|---|---|
| 4,705,616 | 11/1987 | Andresen et al. | 204/299 R |
| 4,842,701 | 6/1989 | Smith et al. | 240/180.1 |
| 4,985,129 | 1/1991 | Burd | 204/299 R |
| 5,037,523 | 8/1991 | Weinberger et al. | 204/299 R |

FOREIGN PATENT DOCUMENTS

| | | | |
|---|---|---|---|
| 339780 | 11/1989 | European Pat. Off. | 204/299 R |
| 339781 | 11/1989 | European Pat. Off. | 204/299 R |

Primary Examiner—John Niebling
Assistant Examiner—John S. Starsiak, Jr.

[57] ABSTRACT

An apparatus for electrophoretic separation comprising a fixed support structure and a cassette shell which is removably attached to the support device. Within the cassette shell is a basket having symmetrically arranged ribs to secure a capillary tube in a helical configuration. The ribs have notches to receive a loop of the helically wound capillary tube. The notches of the ribs alternate in orientation with respect to the axis of the helically wound capillary tube. A quarter-turn locking member provides electrical, optical and coolant fluid communication between the cassette shell and the support device.

16 Claims, 6 Drawing Sheets

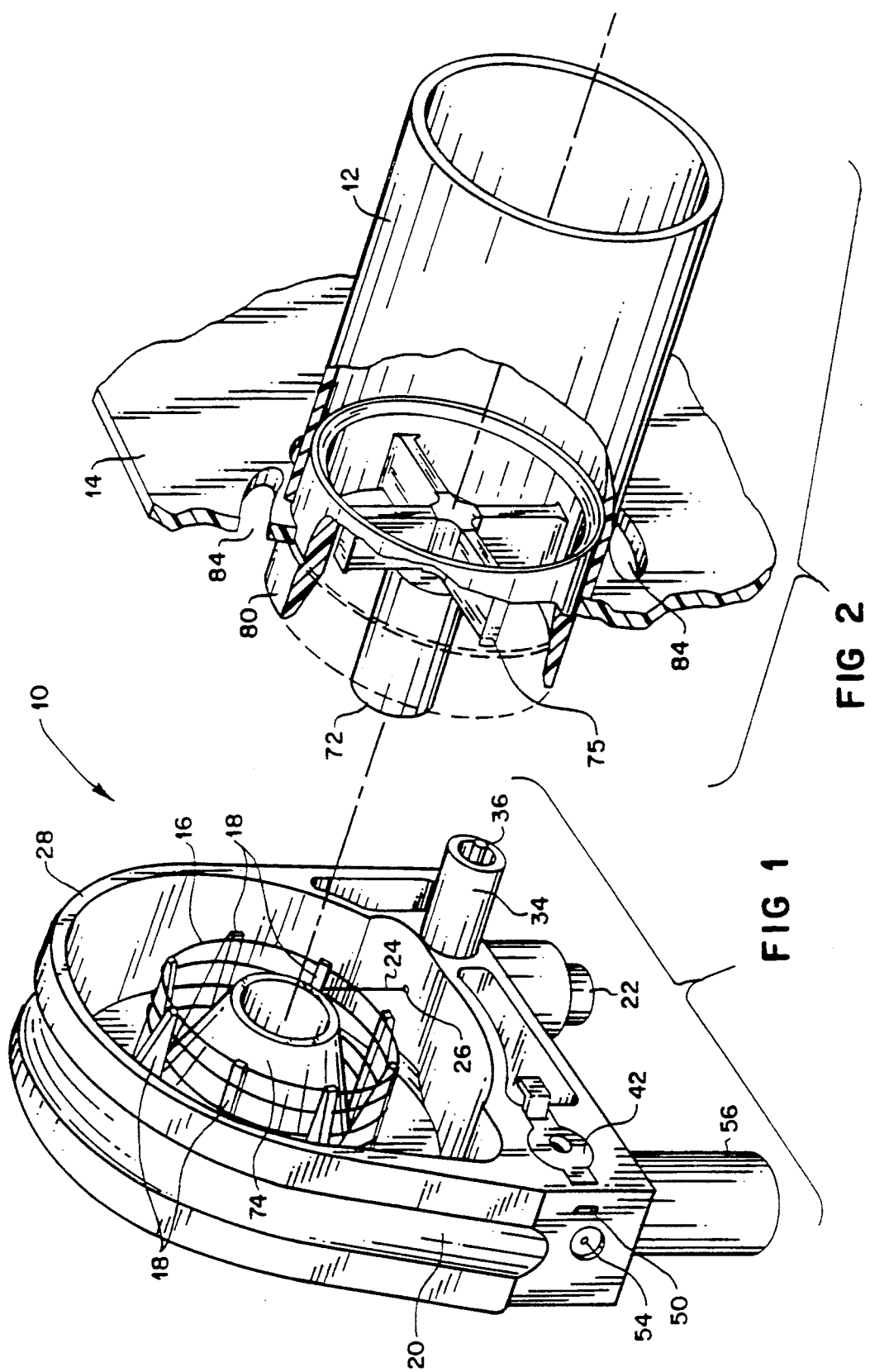

CAPILLARY ZONE ELECTROPHORESIS CASSETTE

TECHNICAL FIELD

The present invention relates generally to electrophoretic processes and particularly to apparatus for performing capillary zone electrophoresis.

BACKGROUND ART

Applications for electrophoresis, an analytical technique for separating and identifying biologically important molecules in a sample, include the determination of a sample's homogeneity, the determination of molecular weights of proteins and nucleic acids, the mapping of nucleic acid primary structures, i.e. DNA and RNA sequence analyses, and the definition of phenotypic variance of a protein at the molecular level. Electrophoretic techniques rely on the fact that each molecular species has a unique combination of mass, size, shape, charge, density and sub-unit structure, all of which result in mobility differences responsive to an electric field. Various electrophoretic techniques use one or more of these properties to cause varying degrees of molecular separation via the migration of the molecular species under a constant or varying electric field.

Capillary zone electrophoresis is a technique using a capillary tube which is filled with a conductive fluid, or buffer solution. A small amount of a sample is introduced at one end of the capillary tube, whereafter a high potential difference is applied across the ends of the tube. Differences in the electrophoretic mobilities of different molecules cause the constituents of the sample to emerge separated at the outlet end of the capillary tube. Capillary zone electrophoresis is described in detail in U.S. Pat. No. 4,842,701 to Smith et al.

Typically, the capillary tube is encased within a linear housing, as shown in U.S. Pat. No. 4,705,616 to Andresen et al. Access to the capillary tube through the encasement is difficult, at best. Yet, access is desirable since capillary tubes have a tendency to clog. A clogged capillary tube normally is not repairable and, therefore, must be replaced.

In addition to the need to periodically repair or replace a clogged capillary tube, free access to the tube is desirable because it permits a change of capillary tubes to best fit an application. As noted above, there are a great number of applications for capillary zone electrophoresis. The operational characteristics of the processes vary with the application. Large diameter electrophoresis capillary tubes permit a greater current flow, but the increased current and the greater susceptibility to convection heating translates into a greater concern for the effects of heating than must be faced in use with small diameter capillary tubes. Heat affects and may even destroy the quantitative and qualitative analysis. On the other hand, use of a small diameter capillary tube makes detection of sample constituents more difficult. As the separated molecular constituents of a sample migrate toward the outlet end of the capillary tube, an electropherogram is obtained by employment of an optical detector. Optimally, the electropherogram shows spaced-apart peaks for the individual constituents of the sample. Small diameter capillary tubes are less conducive to such detection. Thus, the operational characteristics of a particular application are a factor in determining the preferred capillary tube diameter for that application. Likewise, the operational characteristics must be considered in any decision as to the length of the capillary tube for a particular application.

It is an object of the present invention to provide an apparatus for electrophoretic separation in which capillary tubes may be selectively changed by a user without a great expense to or mechanical handling by the user. Another object is to provide such an apparatus in a compact manner.

DISCLOSURE OF THE INVENTION

The above objects have been met by an electrophoretic apparatus which utilizes a compact, freely removable capillary tube wound like a helix. The capillary tube is housed within a cassette shell having walls which define a capillary region with the rear face of the cassette shell to provide access to the capillary region for removal of the tube. In operation, the open rear face is seated against a support structure which houses a power supply, an optical detector and a source of coolant. A lock member is rotated 90° to selectively release the cassette shell from the support structure.

The capillary cassette is mounted within the cassette shell by a plurality of rib members disposed in a symmetrical pattern. Preferably, the rib members are circularly arranged and support the capillary tube in a helical configuration. Each rib member includes a number of notches along one side of the rib member. The capillary tube is a long, resilient member having memory urging the tube to straighten. The resilient capillary tube may be trained in a helix so that individual loops are formed by placement of the tube into the notches. In relation to the axis of the helically wound capillary tube, the rib members are fixed so that the notches alternate in being on the radially inward sides and the radially outward sides of the rib members. Alternatively, the capillary tube may be a rigid member which is fixed in a wound condition.

The cassette shell has a predetermined input pattern of attachments and openings which corresponds to an output pattern on the support structure. The attachments include at least one electrical connection to a power source for supplying a high potential energy necessary to achieve the electrophoretic process. The openings include an aperture for passage of the optical beam used in detecting the flow of molecules. The input pattern further includes the open rear face of the cassette shell which permits entrance and exits of a stream of pressurized gas for controlling the temperature of the capillary tube.

The cassette shell is selectively fastened to the support structure by a locking device which provides a clamping action by a 90° turn of the member. Release of the cassette shell allows free access to the capillary tube through the open rear face. In replacing a capillary tube, the tube is merely unwound from the rib members and the replacement tube is wound in place, whereafter the cassette shell can again be fastened against the support structure.

An advantage of the present invention is that a clogged capillary tube can be readily and inexpensively replaced. Another advantage is that tubes of varying length and diameter can be changed to suit the characteristics of a particular electrophoresis application. Replacement is possible without the changing of structural components other than the capillary tube. Moreover, such replacement can be performed without the aid of tools.

BRIEF DESCRIPTION OF THE DRAWINGS

FIG. 1 is a perspective view of a capillary cassette for supporting a capillary tube in accord with the present invention.

FIG. 2 is perspective view of a support structure for the capillary cassette of FIG. 1.

BEST MODE FOR CARRYING OUT THE INVENTION

Figure 3:
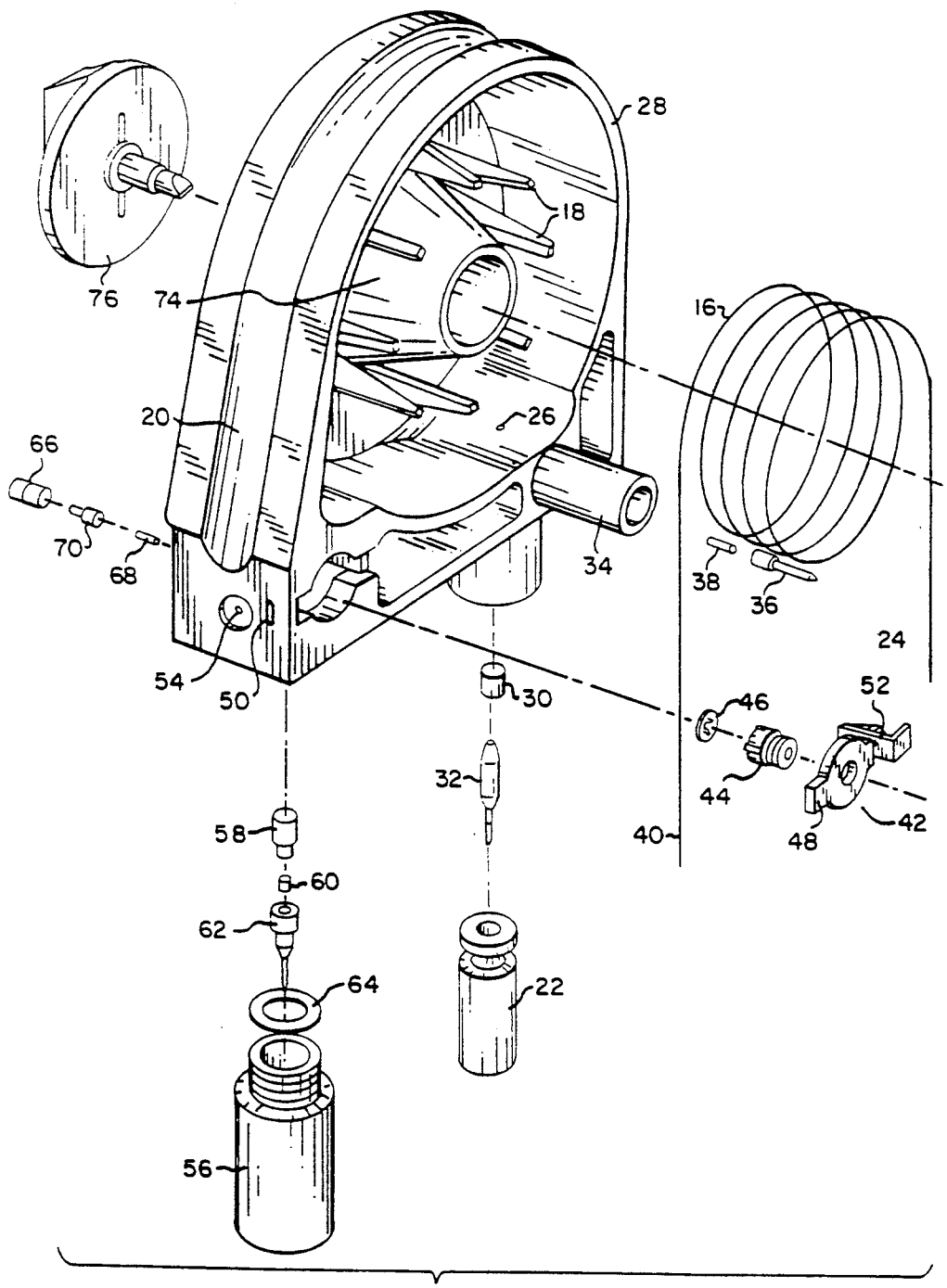
FIG. 3 is an exploded view of the capillary cassette of FIG. 1.

With reference to FIGS. 1 and 2, a capillary cassette 10 is shown in alignment for attachment to a fixed support structure which includes a cylindrical fan housing 12 and a front support wall 14. A capillary tube 16 is maintained in a coiled condition by a capillary basket that includes a series of ribs 18 that alternate in orientation. The capillary cassette 10 is removably attached to the front support wall 14. A groove 20 about the exterior of the capillary cassette facilitates gripping of the member during removal.

In capillary zone electrophoresis, separation of molecules occurs within the capillary tube 16. Referring to FIGS. 1 and 3, a sample vial 22 is attached at an inlet end 24 of the capillary tube 16. The inlet end 24 is inserted into a small diameter bore 26 in a cassette shell 28, then passes through an anode insert 30 for attachment to an anode electrode 32. The capillary tube 16 is filled with a conductive fluid, or buffer, after which a small amount of the sample to be separated is introduced at the inlet end 24 either hydrodynamically or electroosmotically. A d.c. potential of up to 30,000 volts is applied at the anode electrode 32 to provide an electromotive force for separation of molecules. The separation is a result of differences in electrophoretic mobility of the molecules.

A protective sleeve 34 projecting from the cassette shell 28 encases an anode contact 36 and a helical spring 38. The helical spring is metallic and is included to ensure electrical communication between the anode contact 36 and the anode insert 30. Upon mounting of the capillary cassette 10 onto the support structure identified above, the protective sleeve 34 is slidably received within the support wall of the structure and the anode contact 36 is caused to make contact with a source of power.

The construction of the capillary tube 16 is known in the art. Preferably, for the present invention the capillary tube is made of fused-silica. A fused silica tube may be trained into the illustrated helical condition by the ribs 18 of the capillary basket, but such a tube is characterized by a memory which urges return of the capillary tube into a generally straight condition. Typically, the capillary tube has an inside diameter of 50 micron and outside diameter of 375 micron, but these dimensions are not critical. The ribs 18 of the capillary basket accommodate 20 cm to 1 meter long fused-silica capillary tubes. Often the fused-silica is encased within a coating of polyimide. Alternatively, the capillary tube may be a rigid member, manufactured to remain in a fixed, wound condition.

On the preferred embodiment, the polyimide coated, fused-silica capillary tube 16 is cut to a desired length and the inlet end 24 of the capillary tube is brought into fluid communication with the sample vial 22 and into electrical communication with a source of high voltage via the anode contact 36. Approximately 3 cm from an outlet end 40 of the capillary tube 16 a window is formed through the polyimide coating. The outlet end 40 is inserted into the capillary shell 28 and the window is aligned along an optical path provided by an aperture clip 42, an aperture mount having a helical spring 44 and an optical aperture member 46. The combination of the aperture mount and the optical aperture member secures the capillary tube in the desired position. The aperture clip 42 is a snap-in member which allows a user to quickly align and clamp the capillary tube without the use of tools. A projecting end 48 of the aperture clip 42 is received within a seat 50 in the cassette shell 28. The opposite end 52 of the aperture clip is selectively released from the cassette shell by a slight bending action of the member. Each of the members 42, 44 and 46 which seat the outlet end 40 of the capillary tube allow passage of optical detection such as by an ultraviolet absorbance detector.

Adjacent to the seat 50, which receives the projecting end 48 of the aperture clip 42, is a vacuum port 54 which is used in drawing a sample from the sample vial 22. The outlet end 40 of the capillary tube 16 is in fluid communication with a reservoir vial 56. To properly mount the outlet end with the reservoir vial, the capillary tube progresses through a cathode insert 58, a deformable ferrule 60, a cathode electrode 62 and a vacuum seal 64. The cathode electrode 62 is an electrical communication with a cathode connector 66 that is received within a bore, not shown, in the front of the cassette shell 28. A cathode spring 68 biases a plunger 70 and the cathode connector 66 into contact with a member at ground potential relative to the positive potential at the inlet end 24 of the capillary tube.

Referring now to FIGS. 1-3, in attaching the capillary cassette 10 to the support structure which includes the cylindrical fan housing 12 in the front support wall 14, a seating rod 72 of the support structure is received within a frustroconically shaped wall 74 of the capillary cassette. Four radial arms 75 secure the seating rod 72. A locking knob 76, shown in FIG. 3, is inserted into the seating rod of the support structure, whereafter a 90° turn of the locking knob causes fastening of the capillary cassette 10 to the support structure. In connecting the capillary cassette to the support structure, the window in the capillary tube is aligned for optical viewing by an ultraviolet absorbance detector, the anode contact 36 is brought into electrical connection with a source of 30,000 volts, and the capillary tube is positioned to receive a cooling flow of pressurized air generated by a rotary fan, not shown.

As best seen in FIG. 2, the cylindrical fan housing 12 has a projecting wall 80 which extends into the capillary cassette to encircle the capillary tube. The rotary fan generates a stream of pressurized air which enters the capillary zone defined between the projecting wall 80 and the frustroconically shaped wall 74. The gas stream is a transverse flow relative to the capillary tube. That is, the major directional component of the gas flow through the capillary region is perpendicular to the molecular flow through the capillary tube. The stream of gas then follows the wall of the cassette shell 28 for return to the interior of the support structure via crescent-shaped openings 84 in the front support wall 14.

Figure 4:
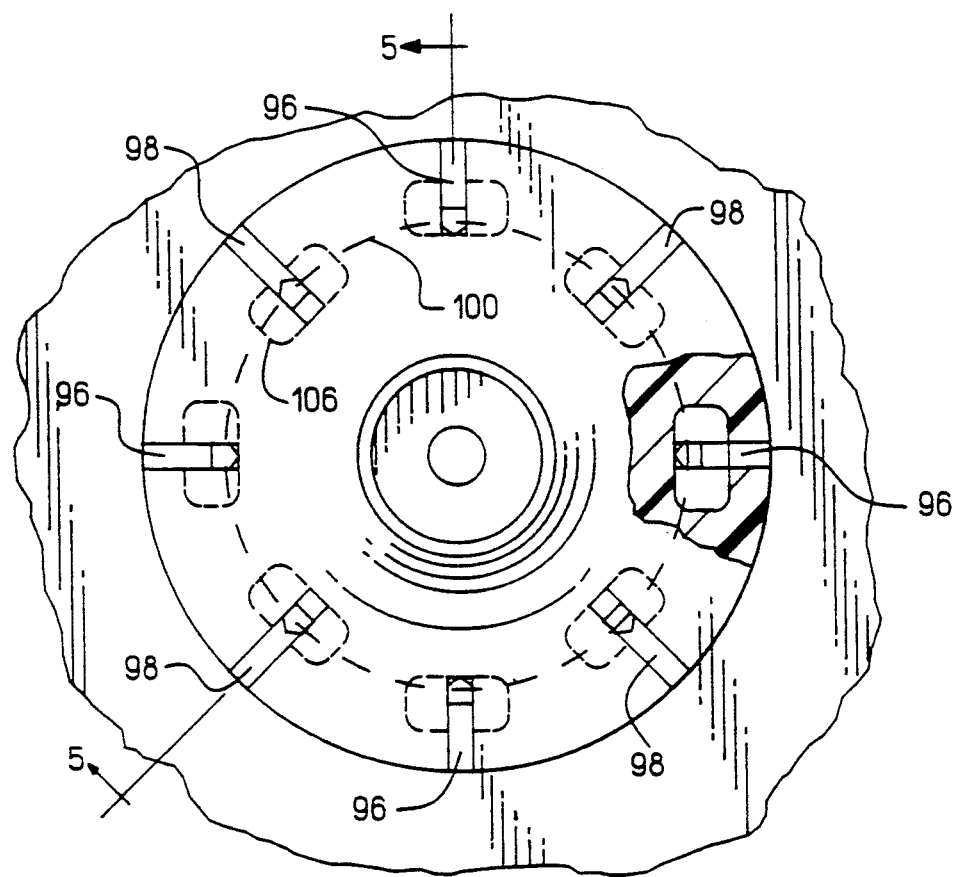
FIG. 4 is a front view of the capillary basket of FIG. 3.
Figure 6:
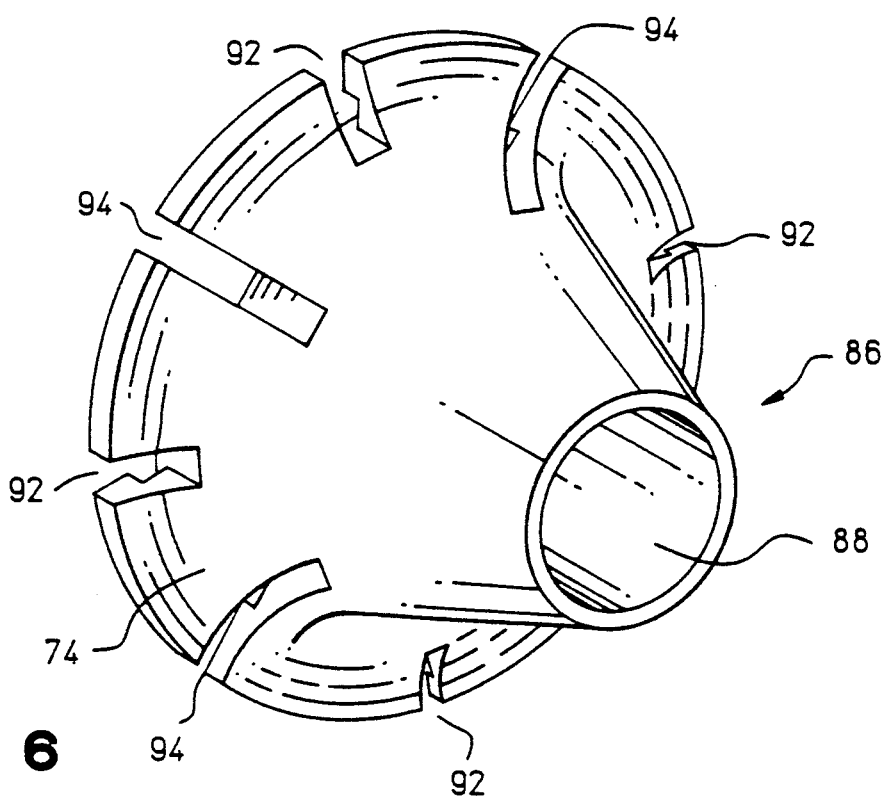
FIG. 6 is a perspective view of the rib retaining member of FIG. 5.
Figure 5:
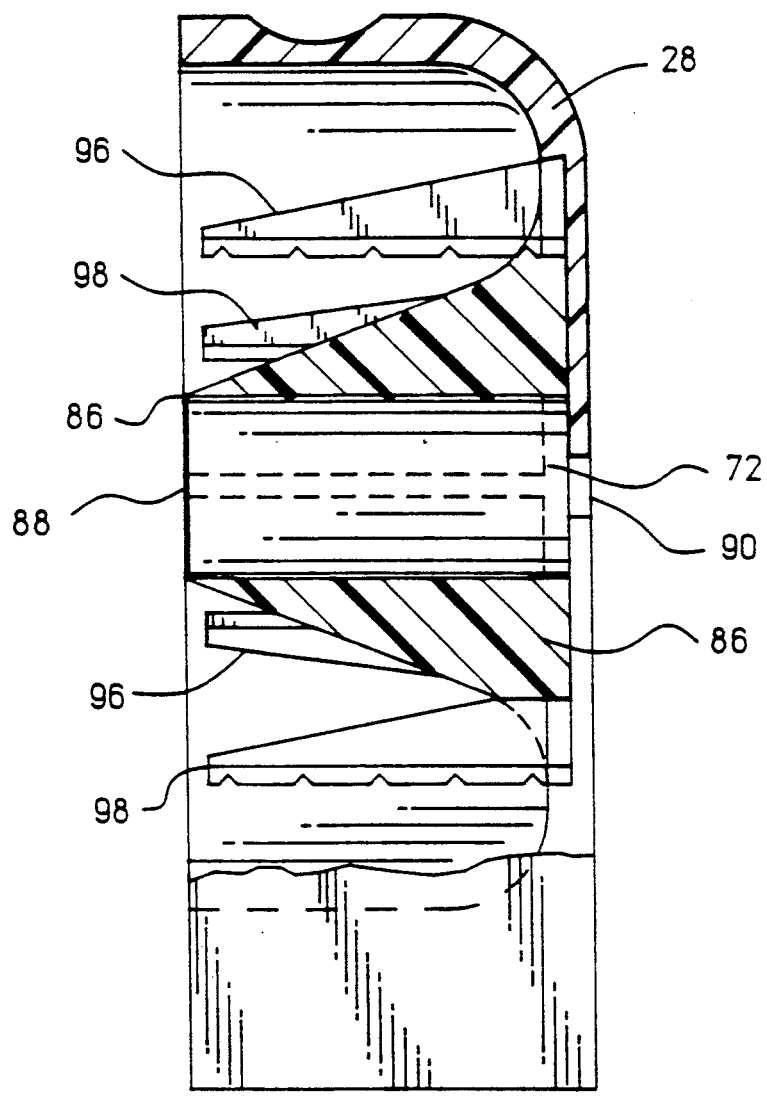
FIG. 5 a side sectional view of the capillary basket of FIG. 4 shown along lines 5—5.

The capillary basket which supports the capillary tube is shown in FIGS. 4-6. A rib-retaining member 86 is fixed to the cassette shell 28 by screws, not shown. Alternatively, the cassette shell 28 may be molded to provide the structure of the rib-retaining member so that a uniform structure is provided. The rib-retaining member 86 includes a center bore 88 which receives the seating rod 72, shown in phantom, of the support structure when the cassette shell 28 is mounted to the support structure. A fastening aperture 90 within the cassette shell permits access to the seating rod 72 for locking the cassette shell to the support structure.

The rib-retaining member 86 defines the frustroconically-shaped wall 74 described above. During an electrophoretic process, pressurized gas from the support structure enters the cassette shell 28 for cooling the capillary tube. The shape of the wall 74 causes a minor redirection of the flow of gas as the flow progresses through the capillary region. Gas molecules which are heated by contact with a first loop of the helically wound capillary tube are forced outwardly by the deflection surface of the frustroconically-shaped wall 74 so as not to come in contact with succeeding loops. This construction promotes uniformity of cooling along the entirety of the capillary tube.

The rib-retaining member 86 includes a series of shallow recesses 92 and deep recesses 94. The shallow recesses 92 alternate with the deep recesses 94, as do the inward-oriented rib members 96 and outward-oriented rib members 98 which are supported within the recesses 92 and 94.

Figure 8:
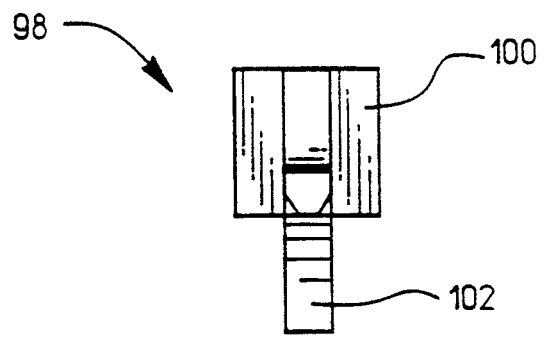
FIGS. 7-9 are various views of a radially inward oriented rib member of FIG. 5.
Figure 7:
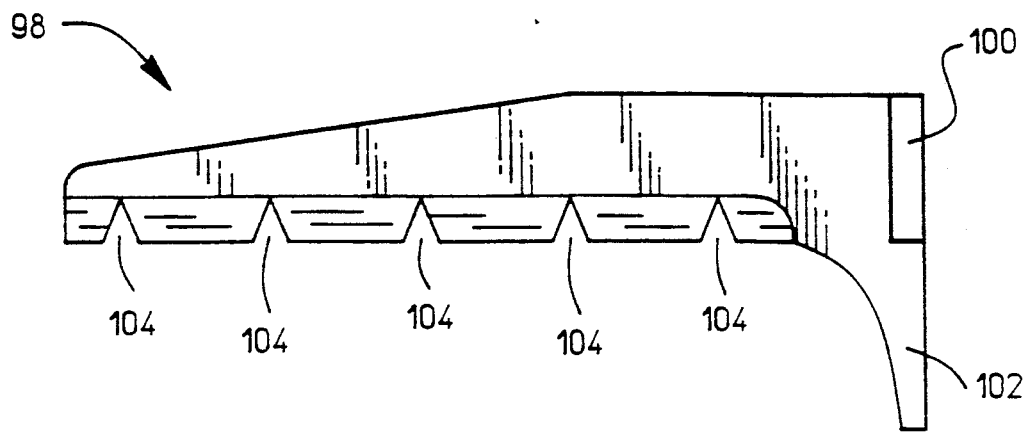
Figure 9:
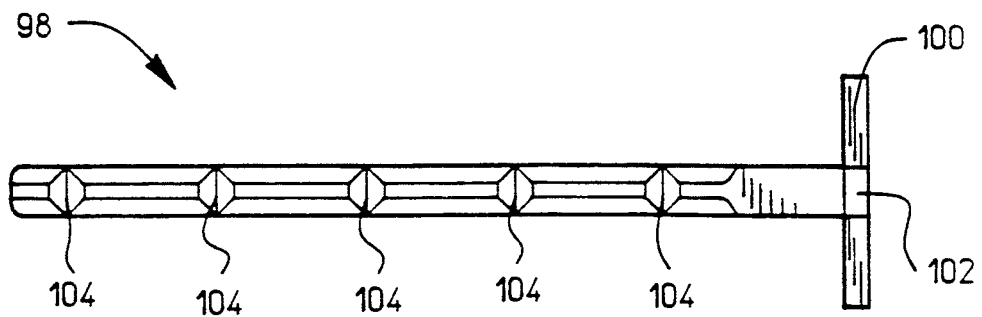

Various views of an outward-oriented rib member 98 are shown in FIGS. 7-9. The rib member 98 includes a foot portion 100 which, when trapped between the rib-retaining member 86 and the cassette shell 98, secures the rib member 98 in position. The base has an extension 102 which follows the contour of the rib-retaining member. The radially inward surface of the rib member 98 includes a series of notches 104. Each notch 104 is adapted to receive a loop of the capillary tube.

Figure 11:
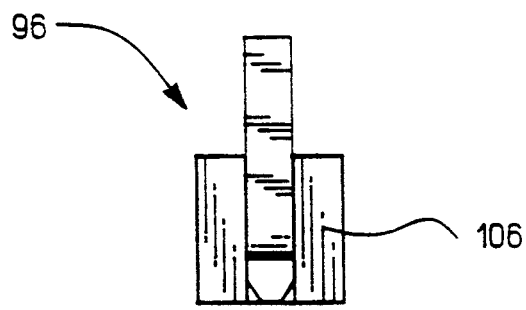
FIGS. 10-12 are various views of a radially outward oriented rib member of FIG. 5.
Figure 10:
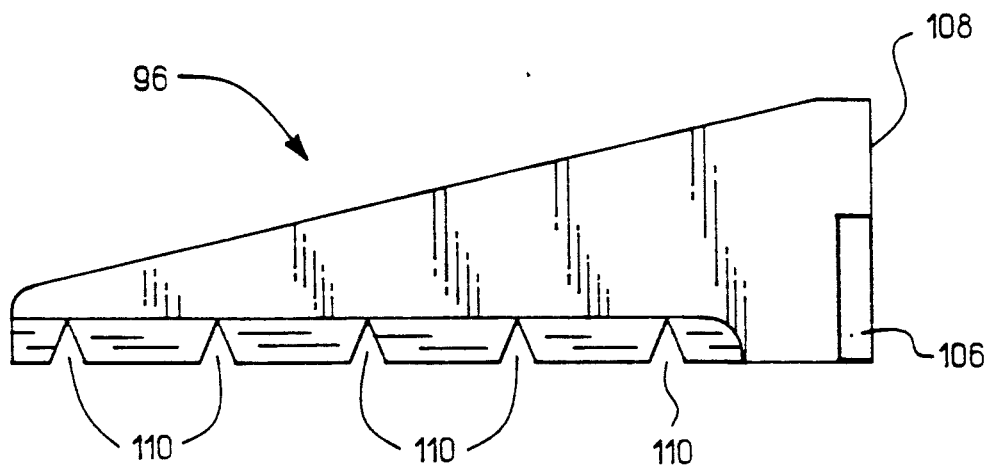
Figure 12:
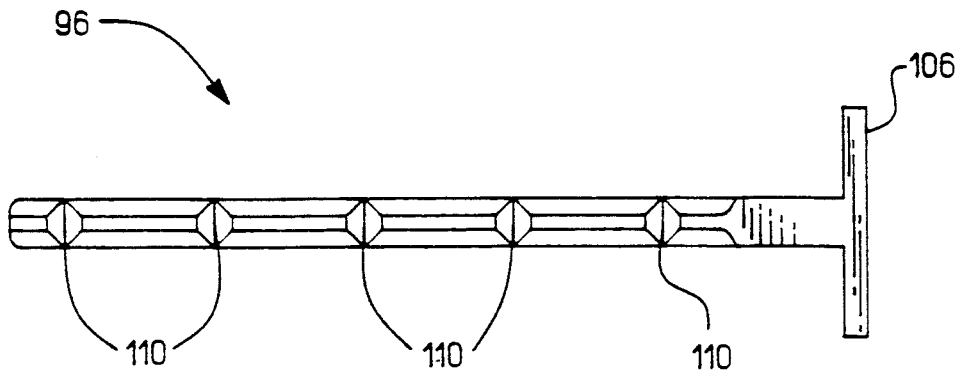

Likewise, the inward-oriented rib member of FIGS. 10-12 has a foot portion 106, a base extension 108 and a plurality of notches 110 to freely receive a loop of a capillary tube. In contrast to the notches of the outward oriented rib members 98, the notches 110 of the rib member 96 are on a surface which faces the axis of the helix formed by the capillary tube.

In operation, the outlet end of a capillary tube 16 is inserted into the cassette shell 28, as shown in FIG. 1. As noted above, the fused-silica tube is characterized by a memory which urges return of the capillary tube into a generally straight condition. The resiliency of the capillary tube is utilized to maintain the tube in a helical configuration. The capillary tube is alternatingly passed radially inwardly and radially outwardly of the ribs 18. The tendency for the capillary tube 16 to expand actually secures the capillary tube in the helical configuration. The inlet end 24 of the capillary tube is then inserted into the small diameter bore 26 of the cassette shell.

Approximately 3 cm from the outlet end of the capillary tube 16, a window is formed through the polyimide coating. The outlet end is inserted into the cassette shell 28 and the window is aligned with an optical path provided by the aperture clip 42. The snap-in clip 42 simultaneously secures the capillary tube to the cassette shell and aligns the tube window for detection of the flow of molecules through the capillary tube. The cassette shell 28 is then pressed against the front wall 14 of the support structure and the quarter turn lock knob clamps the capillary cassette 10 in position. In doing so, the anode contact 36 is electrically joined to a power source. Moreover, the optical detector of the support structure is positioned to direct an optical read beam through the aperture clip 42, and the rotary fan can direct a cooling flow of gas, preferably air, across the capillary tube 16 for return through the crescent-shaped openings 84 in the front wall 14.

The open rear face of the capillary cassette 10 allows a user to change the capillary tube 16 as desired. Replacement of the capillary tube is necessary upon clogging of a tube. The user is also permitted to change the capillary tube according to the characteristics of a particular application. For example, a capillary tube which is 30 cm in length may be preferred for one application, while a length of one meter is preferred in a second application. Selectively changing the capillary tube to provide a desired diameter is also possible.

We claim:

1. An apparatus for electrophoretic separation comprising,
   a cassette shell having walls defining a capillary region therein, said cassette shell adapted to be removably mounted to a support structure,
   an electrophoresis capillary tube releasably mounted to said cassette shell, said capillary tube having a wound center portion within said capillary region and having inlet and outlet ends extending from said capillary region,
   means for selectively fastening said cassette shell to said support structure, said cassette shell having connector means for electrically connecting said inlet and outlet ends to said support structure to provide a high electrical potential difference between said inlet and outlet ends of the capillary tube, and
   a plurality of rib members fixed to said cassette shell for mounting said capillary tube in a wound condition, said rib members disposed in a circular pattern and in contact with said capillary tube, said capillary tube being a resilient member, the resiliency of said capillary tube providing a force urging said capillary tube to remain in contact with said rib members, each rib member having a plurality of notches extending along a side generally coinciding with the direction of the axis of said circular pattern, said notches adapted to receive loops of said capillary tube to form a helix.

2. The apparatus of claim 1 wherein said cassette shell has a front face and has a rear face having an opening therein, said open rear face being in abutting relation with said support structure when said cassette shell is fastened to said support structure, said open rear face providing free access to said capillary region for replacing said capillary tube.

3. The apparatus of claim 2 wherein said open rear face is positioned to receive a flow of pressurized gas from said support structure and to channel said gas for return to said support structure.

4. The apparatus of claim 1 wherein some of said rib members have said notches on a radially inward side of said rib members and some having said notches on a radially outward side.

5. The apparatus of claim 1 wherein said fastening means is a single clamp device.

6. The apparatus of claim 5 wherein said clamp device is a rotatable locking device.

7. An apparatus for electrophoretic separation comprising,
a fixed support device,
a portable cassette shell having a front wall and side walls defining a capillary region and having a rear face, said rear face having an opening to provide access to said capillary region, said cassette shell having a means for selectively clamping said open rear face in abutting relation with said support device,
means coupled to said cassette shell for supporting a capillary tube in a wound condition within said capillary region in a manner to permit the removal of said capillary tube through said open rear face of said cassette shell, and
an electrophoresis capillary tube releasably attached to said support means, said capillary tube having inlet and outlet ends, said cassette shell having electrically conductive contacts in electrical communication with said inlet and outlet ends to provide a high voltage for generating an electrophoresis process within said capillary tube.

8. The apparatus of claim 7 wherein said capillary tube is coiled by said support means to form a helical configuration.

9. The apparatus of claim 8 wherein said support means includes a plurality of spaced apart ribs symmetrically arranged about the axis of said helical configuration.

10. The apparatus of claim 9 wherein said ribs have a plurality of notches to receive said capillary tube, some of said ribs having notches on a radially outward side and being separated by ribs having notches on a radially inward side.

11. The apparatus of claim 7 wherein said clamping device is a lock member rotatably received by said support device.

12. An apparatus for providing electrical, optical and coolant-fluid communication with a capillary tube for electrophoretic separation therein, comprising,
a fixed support device having a front wall having a pattern of openings to permit inflow and outflow of a fluid coolant,
a removably cassette selectively mounted to said support device at said front wall, said cassette having a capillary tube mounted in a wound condition within a capillary region, said cassette having a linear optical path directed at said front wall to receive a detection beam directed therefrom, said optical path intersecting said capillary tube, said cassette having an opening to said capillary region that is in fluid communication with said pattern of openings in said front wall, said cassette having contact means for electrical connection to a high voltage external to said cassette, said contact means in electrical communication with opposed ends of said capillary tube, and
means for selectively fastening said cassette to said support device.

13. The apparatus of claim 12 wherein said capillary tube has an inlet end and an outlet end, said outlet end being secured in position relative to said cassette by a clamp adapted to be snap fit to said cassette.

14. The apparatus of claim 12 wherein said cassette has means for providing fluid communication of the interior of said capillary tube with an external supply of fluid to be electrophoretically separated.

15. The apparatus of claim 12 wherein said capillary tube is wound in a helical configuration.

16. The apparatus of claim 13 wherein said clamp has an aperture within said linear optical path.

* * * * *